United States Patent [19]
Otani

[11] Patent Number: 5,387,182
[45] Date of Patent: Feb. 7, 1995

[54] FAUCET MOUNTED WATER JET DENTAL HYGIENE APPARATUS

[76] Inventor: Tony U. Otani, 12438 Eckleson St., Cerritos, Calif. 90701

[21] Appl. No.: 31,598

[22] Filed: Mar. 15, 1993

[51] Int. Cl.⁶ .............................................. A61H 9/00
[52] U.S. Cl. ................................................. 601/165
[58] Field of Search .................... 433/80; 128/66, 624; 601/165

[56] References Cited

U.S. PATENT DOCUMENTS

| | | | |
|---|---|---|---|
| 3,227,380 | 1/1966 | Pinkston | 128/62 A |
| 3,386,439 | 6/1968 | Harper | 128/66 |
| 3,424,156 | 1/1969 | Smith | 128/62 A |
| 3,468,306 | 9/1969 | Heitzman | 128/66 |
| 3,499,440 | 3/1970 | Gibbs | 128/66 |
| 3,500,824 | 3/1970 | Gilbert | 128/62 A |
| 3,593,707 | 7/1971 | Pifer | 128/62 A |
| 3,690,314 | 9/1972 | Trupp et al. | 128/66 |
| 4,265,229 | 5/1981 | Rice et al. | 128/66 |
| 4,941,459 | 7/1990 | Mather | 128/66 |
| 5,095,893 | 3/1992 | Rawden, Jr. | 128/66 |

OTHER PUBLICATIONS

Best Department Stores Catalog, p. 271, dated Spring 1993 (date is based upon best belief).
Teledyne Water Pik Instruction Manual, dated 1991.
Sunbeam Home Comfort Dental Accessories Order Form, dated 1991.

*Primary Examiner*—Cary E. O'Connor
*Attorney, Agent, or Firm*—Peter D. Keefe

[57] ABSTRACT

A pressurized water jet dental hygiene apparatus which connects to a conventional faucet, composed of a two-component coupling, a flexible tube, and a hand held nozzle connected with the flexible tubing. A first component of the two-component coupling is threaded onto a selected faucet. The second component of the two-component coupling is connected with the flexible tubing. In operation, the faucet operates normally when the second component of the two-component coupling is removed. When it is desired to operate the fluid jet dental hygiene apparatus, the second component of the coupling is connected with the first component. Now, when water is turned on, water will squirt out the nozzle with a velocity and volume dependent upon the water pressure delivered at the faucet and relative amount the faucet valve (or valves) is (are) opened. The user then holds the nozzle such as to provide jetable cleansing of his or her dental tissues.

2 Claims, 1 Drawing Sheet

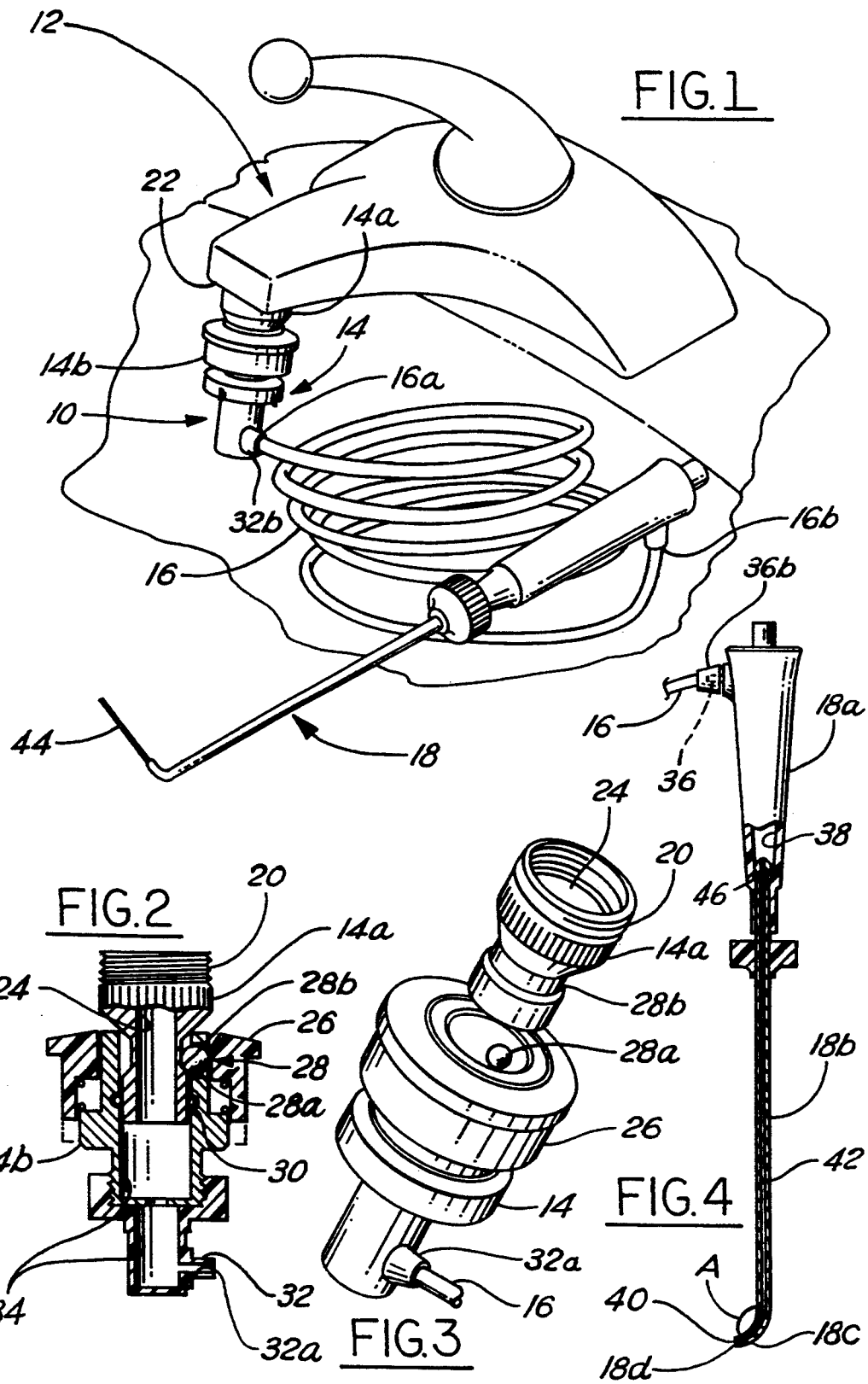

FAUCET MOUNTED WATER JET DENTAL HYGIENE APPARATUS

BACKGROUND OF THE INVENTION

1. Field of the invention

The present invention relates to apparatus for providing a pressurized water stream for dental hygienic cleaning. More particularly, the present invention relates to an apparatus of the aforesaid class which is mounted on a faucet and which derives water stream pressure directly from the drinking water supply.

2. Description of the Prior Art

It is well established that regular and thorough dental cleaning is essential for healthy teeth and gums. Yet, individuals consider brushing and flossing to be an onerous chore that must be repeated day after day.

In response to this public dissatisfaction, a number of dental products have been introduced with varying amounts of success. For instance, new kinds of toothbrush designs, new kinds of toothpaste, dental floss holders, specialized mouthwashes, and electric toothbrushes have been marketed over the years.

One kind of dental hygiene product of great note is that which produces a pressurized fluid jet via a self contained water tank and pump. Examples of such conventional fluid jet products are those manufactured by Teledyne Water Pik under the trademark "WATER PIK", Viadent, Inc. under the trademark "VIA-JET", and Bausch and Lomb under the trademark "INTER-JET". These conventional fluid jet products operate by water (or other fluid) being pumped to a hand-held nozzle which sprays water (or the other fluid) under pressure toward the user's dental tissues. The concept is that the spray will serve to dislodge food and other bacterial hiding places on and between teeth and gums so as to provide a truly clean mouth.

While the conventional fluid jet concept is truly excellent, it suffers from a number of disadvantages. It requires that a bulky pump and tank unit be kept on a counter top of the bathroom; it requires the unit be plugged into a potentially hazardous electrical outlet; and it requires the user to be burdened by set-up and dismantlement.

Accordingly, what is needed in the art is a water jet dental hygiene apparatus which has none of the disadvantages of conventional fluid jet products.

SUMMARY OF THE INVENTION

The present invention is a water jet dental hygiene apparatus which utilizes no tank and no accompanying pump. The water jet dental hygiene apparatus according to the present invention is composed of a two-component coupling, a flexible tube, and a hand held nozzle connected with the flexible tubing. A first component of the two-component coupling is threaded onto a selected faucet. The second component of the two-component coupling is connected with the flexible tubing.

In operation, the faucet operates normally when the second component of the two-component coupling is removed. When it is desired to operate the fluid jet dental hygiene apparatus, the second component of the coupling is connected with the first component. Now, when water is turned on, water will squirt out the nozzle with a velocity and volume dependent upon the water pressure delivered at the faucet and relative amount the faucet valve (or valves) is (are) opened. The user then holds the nozzle such as to provide jetable cleansing of his or her dental tissues.

Accordingly, it is an object of the present invention to provide a water jet dental hygiene apparatus that connects to a conventional faucet and which provides a water jet via the inherent water pressure supplied via the building plumbing lines.

It is an additional object of the present invention to provide a water jet dental hygiene apparatus in which a two-component coupling provides easy connection and disconnection of the nozzle and flexible tubing thereof with respect to a conventional faucet.

These, and additional objects, advantages, features and benefits of the present invention will become apparent from the following specification.

BRIEF DESCRIPTION OF THE DRAWINGS

FIG. 1 is a perspective view of the water jet dental hygiene apparatus according to the present invention, shown in operation with respect to a conventional faucet.

FIG. 2 is a partly sectional side view of the two-component coupling according to the present invention.

FIG. 3 is a perspective detail view of the two-component coupling according to the present invention, showing the two components thereof mutually separated.

FIG. 4 is a partly sectional side view of the hand-held nozzle according to the present invention, seen along lines 4—4 in FIG. 1.

DETAILED DESCRIPTION OF THE PREFERRED EMBODIMENT

Referring now to the Drawing, FIG. 1 shows the water jet dental hygiene apparatus 10 according to the present invention in operation in connection with a conventional faucet 12. As can be discerned from FIG. 1, the water jet dental hygiene apparatus 10 is composed generally of a two-component coupling 14, a flexible tube 16 and a hand-held nozzle 18.

One component 14a of the two-component coupling 14 is provided with threads 20 which threadably engage with threads provided on the spout 22 of the faucet 12. The threads 20 may be external or internal depending on the thread location on the spout 22. The first component 14a has an axial aperture 24 (see FIG. 2) which provides for unobstructed flow of water therethrough in the manner of the spout to which it is attached. The axial aperture 24 may be additionally provided with a conventional aerator/strainer devices commonly used on faucet spouts, which usually include one or more internal rubber gaskets. Preferably, the first component 14a is constructed of corrosion resistant metal having a pleasing, faucet matching finish, but this is not a requirement, as it could be constructed of another corrosion resistant material, such as plastic.

The two-component coupling 14 also includes a second component 14b which is selectively releasable with respect to the first component 14a. Selective releasability may be provided in any conventional manner, such as by a spring loaded plunger 26 which selectively actuates a ball and detent mechanism 28. An annular gasket 30 provides a water tight seal between the second component 14b and the first component 14a when the second component is seated with respect to the first component. In the preferred example shown in FIGS. 1 through 3, the plunger 26 is conveniently pulled down by the user, which effects to free the bail 28a from the detent 28b so as to thereby allow the second component 14b to be pulled free of the first component 14a in one simple movement by the user. The second component 14b is provided with a first connector 32 having a central aperture 32a. Preferably the first connector 32 is side mounted with respect to the second component 14b so as to aid in keeping the flexible tubing 16 away from the nearby basin, which may be filled with unclean water or debris. The second component 14b may be constructed of metal and plastic components, all metal, all plastic, or some other combination of corrosion resistant materials.

The flexible tubing 16 is preferably constructed of a durable, light and resilient plastic material. By way of example, but not limitation, the flexible tubing may be about three-eighths inch in diameter and be about two and one-half feet long. A first end 16a of the flexible tubing 16 is sealably press fit onto the connector 32; and an exterior press fit collar 32b may be provided to clamp the flexible tube to the first connector. The second component 14b is provided with an internal hollow 34 which communicates between the central aperture 32a and the axial aperture 24.

The hand-held nozzle 18 is composed of a handle portion 18a and a nozzle portion 18b, both of which being preferably constructed of rigid plastic material. The nozzle portion 18b is sealably press-fit with respect to the handle portion 18a, thereby allowing periodic replacement of nozzle portions. A gasket 46 facilitates sealing. The handle portion 18a is provided with a second connector 36 having a central aperture (not shown) structured in the manner described relative to the first connector 32. The second end 16b of the flexible tubing 16 is sealably press fit onto the second connector 36, an external collar 36b being optionally utilized as a clamp. The handle portion 18a is provided with an internal cavity 38 which communicates with the central aperture of the second connector 36.

The nozzle portion 18b is preferably shaped in the form of a narrow tube, having a turned end piece 18c. The turn angle A is largely a matter of choice, but a desirable range thereof is from between 90 and 150 degrees, and could even be 180 degrees (i.e., no turned end piece being present). The tip 18d is preferably provided with a narrowing taper. An orifice 40 at the tip 18d preferably has a reduced cross-section from the nozzle passage 42 as a result of the aforesaid taper of the tip, although this is not a requirement. The nozzle passage 42 communicates with the internal cavity 38. The diameter, shape and over-all structure of the orifice 40 determines the spray velocity given a preset water pressure and flow rate; it also determines the shape of the spray 44. Accordingly, the orifice 40 is preferably predetermined to provide an optimum spray for dental hygiene purposes.

In operation, the user installs the water jet dental hygiene apparatus 10 by first threading the first component 14a of the two-component coupling onto a selected faucet. The faucet will thereupon operate and deliver water in an entirely normal manner through the first component. When the user wishes to clean his or her teeth, the second component 14b of the two-component coupling is pressed into sealably seated engagement with the first component. Now, when water is turned on at the faucet, the water therefrom will spray out of the orifice at the nozzle portion of the hand-held nozzle. The flexible tubing allows the user to easily manipulate the spray as needed to secure a full and complete oral cleaning. The spray flow rate, pressure and over-all quality will be dependent upon the water supply to the faucet and how much the user has opened one or more of the faucet valves, which may or may not involve mixing of hot and cold water so as to provide a pleasing spray temperature.

When the dental hygiene session is completed, the plunger is pulled so as to disengage the second component from the first component of the two-component coupling, and the flexible tubing and hand-held nozzle are thereupon stored for the next dental hygiene session.

It should be noted that while it is understood that conventional fluid jet products provide a pulsating spray, this is not believed to be necessary for providing a thorough cleansing action to the dental tissues of the user. Accordingly, the continuous spray produced from the faucet will more than adequately cleanse the user's dental tissues in a most thorough manner.

To those skilled in the art to which this invention appertains, the above described preferred embodiment may be subject to change or modification. Such change or modification can be carried out without departing from the scope of the invention, which is intended to be limited only by the scope of the appended claims.

What is claimed is:

1. A water jet dental hygiene apparatus for being connected with a spout of a faucet having at least one valve, said water jet dental hygiene apparatus comprising:

a two-component coupling, comprising:

a first component having a threaded portion for being threadably engaged with the spout of the faucet, said first component having an axial aperture;

a second component having a blind internal hollow, said blind internal hollow having an open end and a blind end, said blind end of said blind internal hollow being permanently sealably closed, said second component having a first connector connected thereto, said first connector having a first central aperture communicating with said blind internal hollow between said open and blind ends thereof; and selectively releasable connection means for sealably seating said second component with respect to said first component, said open end of said blind internal hollow communicating with said axial aperture when said first component is sealably seated with respect to said second component; said selectively releasably connection means comprising:

a plunger movably connected with respect to said second component between a first position and a second position;

biasing means connected with said second component for resiliently biasing said plunger toward said first position; and ball and detent means connected with said first and second components, wherein said ball and detent means provides selective connection of said first component responsive to movement of said plunger component responsive to movement of said plunger between said first position and said second position;

a flexible tube having a first end and a second end, said first end of said flexible tube being connected with said first connector; and a hand-held nozzle, comprising:

a handle portion having an internal cavity, said handle portion having connected thereto a second connector, said second connector having a second central aperture communicating with said internal cavity, said second end of said flexible tube being connected with said second connector; and a nozzle portion sealably connected with said handle portion, said nozzle portion having a nozzle passage therealong which communicates with said internal cavity, said nozzle portion having a tip, said tip having an orifice for providing therefrom a water jet spray when the at least one valve of the faucet is opened.

2. The water jet dental hygiene apparatus of claim 1, wherein said nozzle portion is selectively releasable with respect to said handle component.

* * * * *